United States Patent [19]
Barnard et al.

[11] Patent Number: 5,386,293
[45] Date of Patent: Jan. 31, 1995

[54] SEAM INSPECTION DEVICE

[76] Inventors: Ronald G. Barnard, 36 Tanglewood Rd., Albany, N.Y. 12205; William H. Creitz, 120 W. Main St., Cambridge, N.Y. 12816

[21] Appl. No.: 200,284

[22] Filed: Feb. 22, 1994

[51] Int. Cl.$^6$ ............................................. G01N 21/90
[52] U.S. Cl. .................................... 356/397; 356/237; 348/92; 348/125; 348/131
[58] Field of Search ........................ 356/394, 397, 237; 348/92, 125, 129, 130, 131

[56]  References Cited
U.S. PATENT DOCUMENTS

| | | | |
|---|---|---|---|
| 5,017,795 | 5/1991 | Dower et al. | 356/385 |
| 5,104,226 | 4/1992 | Eble et al. | 356/237 |
| 5,260,766 | 11/1993 | Armitage | 348/125 |

*Primary Examiner*—F. L. Evans
*Attorney, Agent, or Firm*—Heslin & Rothenberg

[57]  ABSTRACT

A video seam inspection device includes a video imaging device, a support for a container along an optical axis of the video imaging device and independent light means for illuminating a seam on the container. The two light means include a side light source and a direct light source. The direct light source may be used to transmit light through a ring illuminator which reflects light off a mirror located along the optical axis of the video imaging device. A side light source transmits light to a light transmission means which focuses the light towards the seam of the container at an angle different from the angle of light from the ring illuminator. A can having a cut-out section of the bottom is placed on the support such that the cross-section of the can is exposed and illuminated by each of the light means. The video imaging device then transmits an image of the seam to a display device.

10 Claims, 3 Drawing Sheets

SEAM INSPECTION DEVICE

BACKGROUND OF THE INVENTION

The present invention relates to a can seam inspection device and, more particularly to an improved optical seam inspection device which provides increased inspection performance due to improved illumination methods.

The purpose of a can seam inspection device is to accurately measure the component parts of a double seam as is typically found around the top of a normal soup-type can. Traditionally, seam measurements were taken by tearing the seams down into their components parts and measuring them with a seam micrometer. This method has been used for many years and is still used regularly in canning plants having low product volume. Seam micrometers are limited, however, in that the positioning of parts therein may vary and thus affects readings, that part measurements vary from inspector to inspector due to slight and varying deformations of the part caused by personal differences in micrometer pressure. Seam micrometers are also time consuming and not practical for high volume production inspection.

An improvement on the traditional method has come in the form of video-based can seam inspection devices which display magnified images of specially prepared seam cross-sections on a video screen or computer monitor where they are measured with video cross-hairs or cursor lines that have been calibrated to measurement units. A video-based can seam inspection device consists mainly of three groups of components: optical, electrical, and mechanical. The optical group comprises a video camera, a magnifying lens, a light source, and a mirror, and in some cases a fiber optic light pipe. The camera and magnifying lens are located toward the back of the device and point directly toward the front of the device where the mirror is located. The mirror is mounted vertically and is angled 45 degrees with respect to the front of the device so that it allows the camera to look 90 degrees to the side of the device. The optical axis of the camera and magnifying lens are coincidental and also pass through the center of the mirror. A small light source is located near the optical axis such that it casts light in a direction essentially parallel to the optical axis and toward the mirror. In some conventional can seam inspection devices a fiber optic light pipe is used to convey the light from a light source to a point near the optical axis instead of placing the light itself near the axis. The electrical group comprises a power supply which powers the light source, and in some devices, also the camera. The mechanical group comprises a base, a mirror mount, a can platform, and an enclosure. The camera and magnifying lens are attached to the base toward the back of the device. The mirror mount holds the mirror in a fixed orientation protruding out slightly from the front of the base and is attached to the front of the base at a height centered about the optical axis of the device. The can platform is also attached to the front of the base in an orientation which is essentially horizontal and parallel to the optical axis and at a height at which a can seam sample is visible to the camera when a can is placed on the platform. The enclosure enshrouds all components except for the can platform, the mirror mount and mirror. It serves to protect the internal components and also shields the camera from stray light. In practice, to perform measurements, a prepared can is placed on the platform so that the seam is visible to the camera. The light source casts predominantly direct light on the seam via the mirror thus illuminating the seam. The illuminated seam reflects light back via the mirror to the magnifying lens and camera which picks up the enlarged image and transmits it to either a video screen or a computer monitor where it is measured with video cross-hairs or line cursors.

The conventional video-based measurement method has clear advantages over traditional methods since it does not measure through contact of the part, so is not subject to the same problems of part positioning or measurement pressure with its resulting part deformation. Measurement accuracy is improved as is inspection efficiency.

Although the conventional video-based can seam inspection device has clear advantages over traditional methods, there are several drawbacks which stem from the prior art's dependence on predominantly direct illumination. These drawbacks affect the accuracy of the device and its use over a wide range of materials. An ideally prepared seam is perfectly flat across its surface, uniformly reflective and composed of metal. Although direct illumination is very appropriate in this situation, it becomes less appropriate the further the seam departs from ideal. Due to the quality of the saws used in the preparation of seam samples, many prepared seams have rounded or nicked edges that make the seam appear smaller under direct illumination. Still other seams, containing regions with disparate reflectivities, such as plastic or composite seams, when viewed under direct illumination, lack enough definition to reveal key edges of the seam components, thus can not be measured at all. Also, in situations where a seam must be analyzed for attributes other than dimensional, as in a visual inspection, direct illumination severely limits visual cues that reveal surface detail and texture.

It is therefore the object of the present invention to provide an improved video-based can seam inspection device which utilizes improved illumination methods that both provide increased measurement accuracy and add the capability of the device to effectively measure non-metallic seams.

SUMMARY OF THE INVENTION

The aforementioned objects may be achieved by a seam inspection device constructed in accordance with the principles of the present invention. The seam inspection device includes an optical display device, a means for supporting a container along an optical axis of the video imaging device, and a dual means for illuminating a seam on the container.

The dual means for illuminating a seam on the container may include a side light source and a direct light source. The optical display device may comprise a video imaging device. A mirror may be located along the optical axis of the video imaging device and oriented at a forty-five degree angle relative to the optical axis. The means for supporting a container along the optical axis should allow the mirror to be placed within the can to allow an image of the seam to be obtained from the reflection off the mirror.

The direct light source illuminates the seam of the container with light directed substantially ninety degrees from the seam. The side light source illuminates the seam of the container with light directed substantially oriented at a shallow angle to the seam.

The direct light source may be oriented to transmit light to a ring illuminator. The ring illuminator may be coaxially positioned relative to the optical axis to transmit a ring of light towards the seam of the container. The ring of light may be reflected off the mirror towards the seam of the container.

The side light source may be oriented to transmit light to a light transmission means capable of transmitting light from the side light source towards the seam of the container at an angle not normal to the seam. The light transmission means may include a fiber optic light transmitter.

The side light source and direct light source may be controlled by a means for independently varying the intensity of the side light source and direct light source. The means for independently varying the intensity of the side light source and direct light source may include a power supply.

BRIEF DESCRIPTION OF THE DRAWINGS

The aforementioned objects, features and advantages of the invention are indicated in the drawings in which.

DETAILED DESCRIPTION OF THE PREFERRED EMBODIMENTS

In accordance with the present invention, the video-based can seam inspection device includes three groups of components: optical, electrical, and mechanical. The optical group comprises a video camera, a magnifying lens, a direct light source, a side light source, a ring illuminator, a light pipe, and a mirror.

Figure 1:
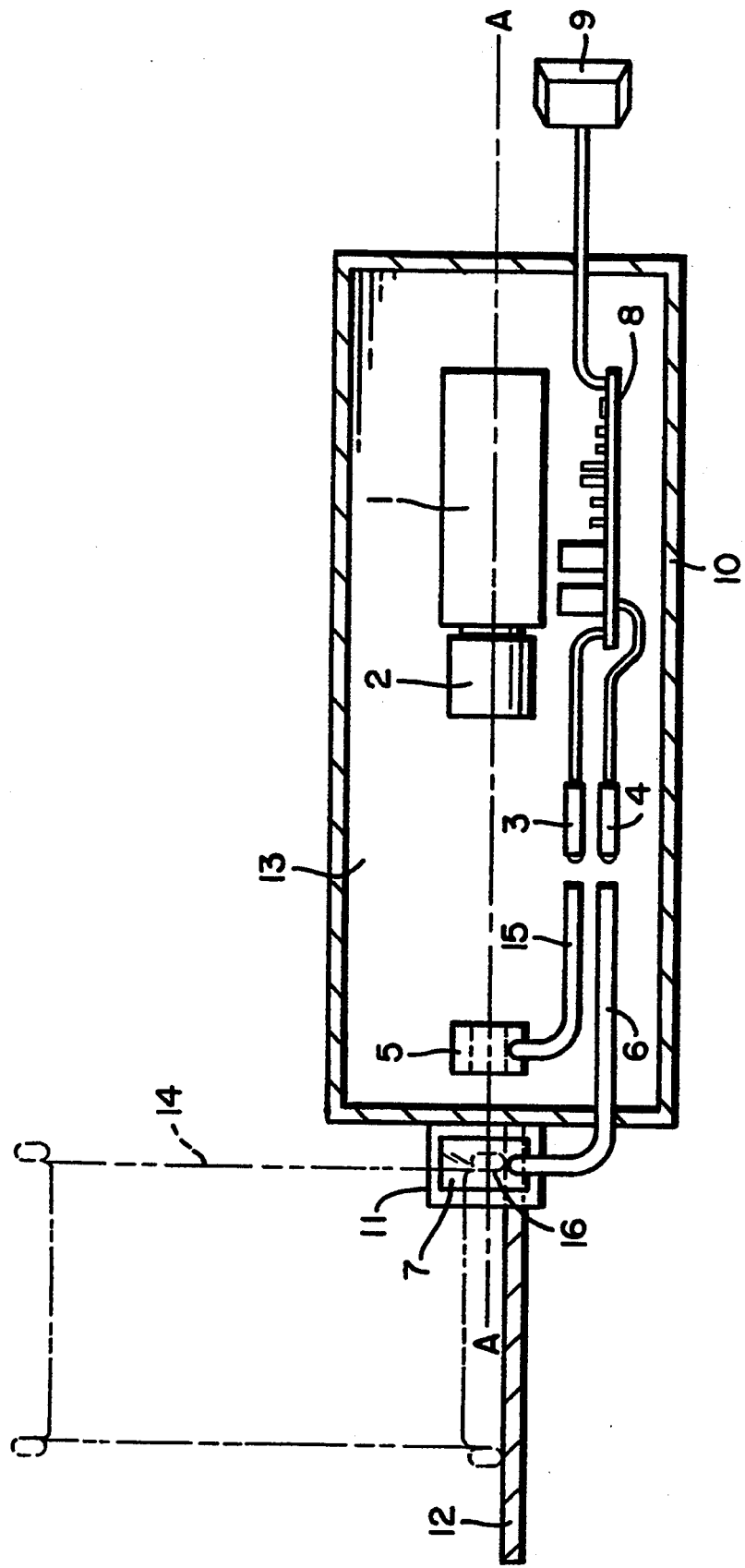
FIG. 1 is a side view of the video-based seam inspection device in accordance with the present invention.
Figure 2:
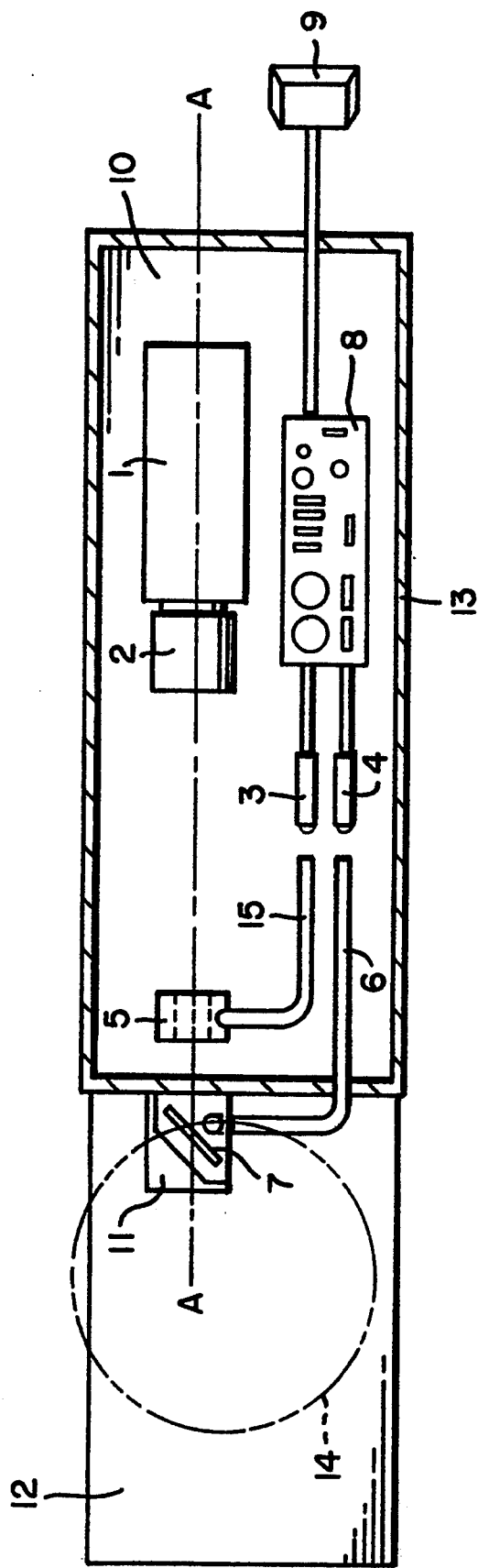
FIG. 2 is a top view of the video-based seam inspection device in accordance with the present invention.
Figure 3:
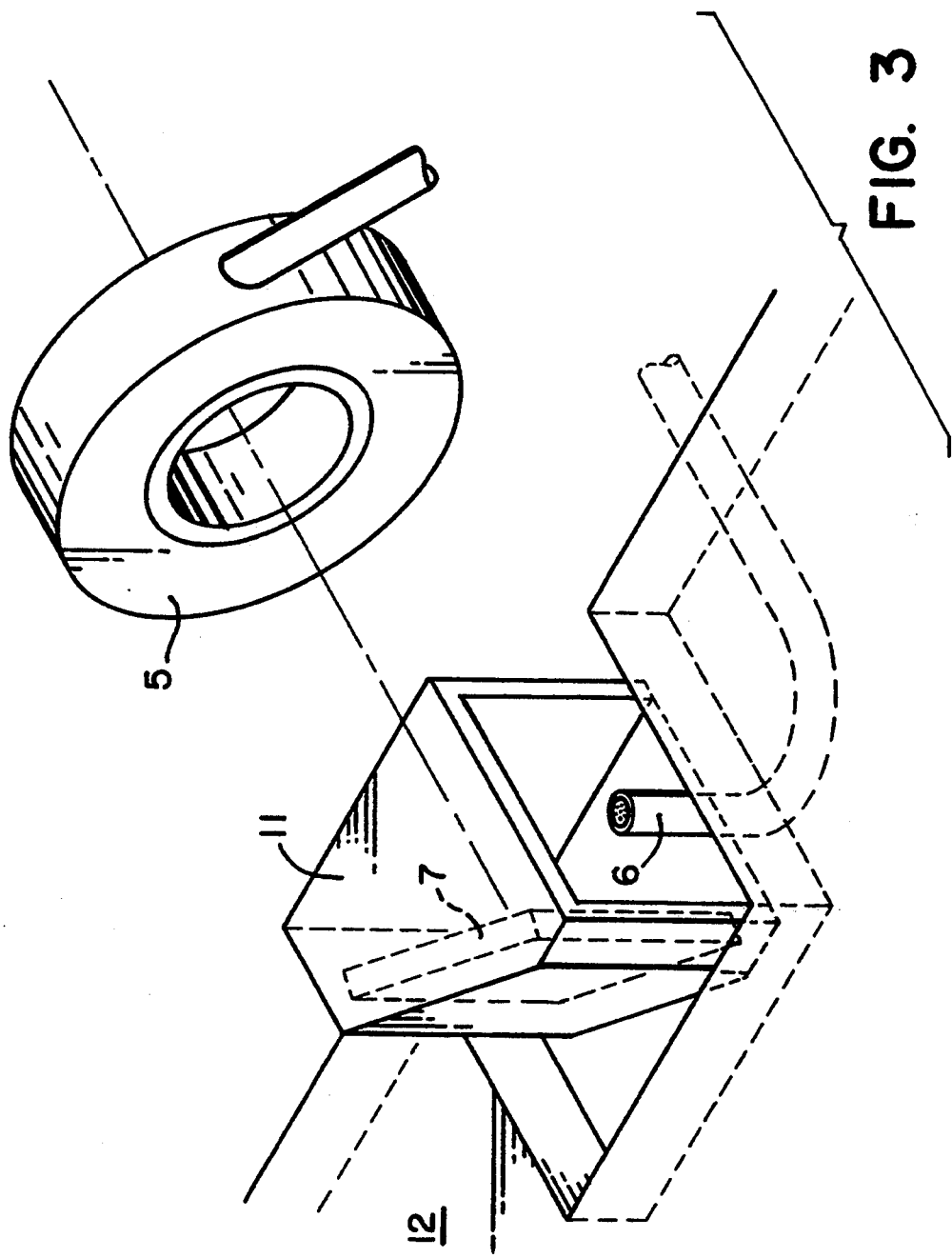
FIG. 3 is a schematic representation of the ring illuminator, mirror mount, mirror, platform, and output end of the light pipe in relation to the optical axis A—A.

Referring to FIG. 1 and 2, the camera 1 and magnifying lens 2 may be located toward the rear of the device and point directly toward the front of the device where the mirror 7 is located. The optical axis A—A of the camera 1 and magnifying lens 2 are coincidental and also pass through the center of the mirror 7. The mirror is mounted vertically and is angled 45 degrees with respect to optical axis A—A so that it allows the camera to focus its image 90 degrees from the optical axis A—A. The ring illuminator 5 is located toward the front of the device and is positioned such that its central axis is coincidental with and coaxial with the optical axis A—A of the camera and its radiant side directed forward toward the mirror essentially parallel to the optical axis. The ring illuminator 5 radiates a ring of light coaxial with optical axis A—A to mirror 7. The center of the ring illuminator 5 is hollow to allow the camera 1 a clear view through it to the mirror 7. A direct light source 3 is positioned at the input end of the ring illuminator's input cable 15 such that its light is directed into the cable. A light pipe 6 is located towards the front of the device with its output end located within the mirror mount 11 towards the object side of the mirror 7 and slightly below the optical axis A—A and is positioned such that its radiant axis points upward and away from the mirror at an inclination angle slightly off vertical (FIG. 3). The input end of the light pipe 6 is located some place within the device. The side light source 4 is positioned at the input end of the light pipe 6 such that its light is directed into the input end of the light pipe 6.

The electrical group comprises a dual voltage power supply 8 and a computer interface 9. The dual voltage power supply powers the two light sources. The computer interface 9 is connected to the dual voltage power supply 8, and in operation, to a computer (not shown) in order to provide power commands.

The mechanical group comprises a base 10, a mirror mount 11, a can platform 12, and an enclosure 13. The camera 1 and magnifying lens 2 are attached to the base 10 toward the back of the device. The ring illuminator 5 and the light pipe 6 are attached to the base near the front of the device. The mirror mount 11 holds the mirror in a fixed orientation protruding out slightly from the front of the base and is attached to the front of the base at a height centered about the optical axis of the device. The can platform 12 may also be attached to the front of the base in an orientation which is essentially horizontal and parallel to the optical axis and at a height at which a can seam sample is visible to the camera when a can is placed on the platform. The enclosure 13 enshrouds all components except for the can platform 12, mirror mount 11, mirror 7 and the output end of the light pipe 6. It serves to protect the internal components and also shields the camera 1 from stray light. In practice, to perform measurements, a prepared can is placed on the platform 12 so that the seam is visible to the camera. The two light sources 3,4 convey light via the ring illuminator 5 and the light pipe casting a combination of both direct and side light on the seam. The illuminated seam reflects light back via the mirror to the magnifying lens and camera which picks up the enlarged image and transmits it to either a video screen or a computer monitor where it is measured with video cross-hairs or line cursors.

The improved video-based seam inspection device in accordance with the present invention contains several advantageous features. The ring illuminator 5 provides more uniform illumination than a single light source placed near the optical axis A—A because it is an area source not a point source of light. The side light source and its associated light pipe provide illumination at a shallow angle to the seam which effectively accentuates the detail and texture in the image. One of the advantages of this device in accordance with the invention, is that each light source 3,4, i.e., the side and direct illuminator, may be independently varied. This independent light source variation allows for the optical illumination of each scene by adjusting the intensity of the side light source 4 and direct light source 3. The low angle light from the light pipe working in concert with the direct light from the ring illuminator 5 can provide a mixed lighting situation which is superior to either alone. The low angle light intensity from the light pipe 6 and the direct light intensity from the ring illuminator 5 can be independently varied to provide the optimum lighting mixture for a given inspection situation. The low angle light intensity and the direct light intensity can be controlled by a computer via the computer interface 9 making it possible to store and instantly recall light settings appropriate for a given inspection situation.

FIGS. 1 and 2 indicate an embodiment of the present invention as incorporated in a video-based seam inspection device. The device comprises a base 10, a mirror mount 11, a can platform 12, an enclosure 13, a video camera 1, a magnifying lens 2, a ring illuminator 5, a light pipe 6, a mirror 7, a direct light source 3, a side light source 4, a dual voltage power supply 8, and a computer interface 9.

The base 10 runs the full length and width of the enclosed portion of the device and is the one part to which all other components are fastened and in this capacity serves its most important function as the foundation for the optical axis A—A. It may be composed of a metal alloy and be thick enough to hold all parts attached to it in a fixed alignment. The base may be blackened with a dull finish either through anodization or flat finish painting in order to reduce the possibility of any reflective glare or stray light entering into the video camera 1.

The optical axis A—A may be parallel with the top of the base 10 and at right angles to the front and rear edges of the base. The optical axis is preferably established by optical centerline of the video camera 1 at the rear of the device and the center of the mirror 7 at the front of the device.

The video camera 1 is preferably attached to the base toward the back of the device and points along the optical axis A—A directly toward the front of the device where the mirror 7 is located. The camera 1 is preferably a self-contained solid state device, preferably a high resolution CCD variety with an array of $510 \times 492$ picture elements or better and a format of $\frac{2}{3}''$ or $\frac{1}{2}''$, such as the SONY model XC-57 or the Cohu model 3310. The CCD variety is preferred over the tube variety for a number of reasons including greater accuracy, less image distortion, higher impact and vibration resistance, and small size. The camera 1 is preferably powered by either 12 Vdc or 12 Vac depending on the variety and should include its own internal voltage regulation. The output video signal may be obtained from a standard video connector located on the back end of the camera. The camera is also fitted with C-mount threads at its front to accept stock lenses or adapters such as extension tubes.

The magnifying lens 2 may preferably be a multiple element CCTV or enlarging lens designed for either $\frac{2}{3}''$ or $\frac{1}{2}''$ format cameras fitted with C-mount threads. However, other types of lenses may be used. It should have an aperture adjustment ring for the final light sensitivity adjustment of the seam inspection device. The lens 2 is attached to either the video camera 1 or to the base 10 at a distance in front of the image plane of the camera that will achieve the desired magnification (approximately $50 \times$). The effective magnification of the device will be found to be the product of two ratios: object distance/image distance and screen size/imager size, where the object distance is the distance from the object (in this case, the sample seam) to the front principle point of the lens, the image distance is the distance from the rear principle point of the lens to imager (light sensitive pickup array) of the camera, and where the screen size is the diagonal measure of the display device, and the imager size is the diagonal measure of the camera's imager. The magnifying lens must also be positioned so that its optical axis coincides with the optical axis A—A of the device. It can be attached to the camera using its C-mount threads or if it is to be mounted an appreciable distance in front of the camera, it can be mounted to a lens mount which is firmly attached to the base 10.

The ring illuminator 5 may be a cylindrically shaped assembly whose central axis coincides with the optical axis A—A and whose front face faces the mirror 7. Ring illuminator 5 may comprise a substantial number of optical fibers encased in a metal shell that determines their orientation and configuration. On the front face, the output end of the optical fibers are arranged to form a thin circular ring whose included fibers are constrained to point in a direction toward the mirror and parallel to the optical axis A—A. Also, the ring illuminator may comprise a ring shaped light such as a fluorescent light. The area of the assembly inside the ring is hollowed out to allow the video camera 1 a clear view through it to the mirror. The inside The inside surface of the hollow may be dulled to discourage unwanted reflections. The input end of the optical fibers exit through the side of the assembly as a single tightly packed group called the input cable 15 which for protection is encased in a rigid or flexible hose-like casing. Optimally, the diameter of the fiber bundle at the input tail should be sized to be approximately equal to the diameter of the input light beam it is expected to receive. The input end of the input cable 15 is placed so that its axis coincides with that of the radiant axis of the direct light source 3. The preferred material for the assembly's metal shell is a non-corrosive stainless steel alloy since it may come in contact acidic or salty foods. However, other materials may be used. The ring illuminator 5 is securely attached to the base between the magnifying lens 2 and the mirror 7 and is oriented so that its axis coincides with the optical axis A—A and is placed at a distance from the mirror that will afford the mirror the most uniform illumination. The use of a ring illuminator as a source of direct lighting is particularly advantageous, especially when viewing metallic samples. Conventional video-based seam inspection devices use primarily a single direct light source which, since it approximates a point source of light, causes illumination problems such as glare, "hot" spots, and dark undefined areas which hinder accurate inspection. A ring illuminator properly placed will reduce these problems since the light it casts is not point based and produces a wider and more evenly distributed area of light.

The mirror 7 is preferably a front surface mirror formed of thin crown glass with a reflective metal coating deposited on its front surface. The mirror 7 may be either square or circular in shape and should have a minimum width of at least three times the length of the largest seam the device will be used to inspect. The mirror 7 may be held by the mirror mount 11 at the front of the device where it is oriented vertically with respect to the base 10, angled 45 degrees with respect to the front of the device in a way that allows the camera to focus on an object located 90 degrees to the side of the device, and positioned so that the optical axis A—A passes through its center. The mirror is permanently attached to the mirror mount with adhesives and has its reflective surface facing out.

The mirror mount 11 may be an approximately cube-shaped part with four solid faces, its top, front, left side, and bottom. Its rear face and right side have been cut away forming a diagonal inside face which rests at a 45 degree angle to both the rear and right side. This inside face forms the mounting surface for the mirror 7 where the mirror is permanently attached with adhesives. The mirror mount 11 may be fixedly attached to the front of the base so that it protrudes out from the enclosed portion of the device. It is mounted at a height and position that allows the optical axis A—A to pass through the center of the mirror. To facilitate easy placement of a can, the corner formed by the junction of the front and left side of the mirror mount can be cut away as shown in FIG. 2, thus leaving a sloping left side. The mirror mount may be preferably made of stainless steel for wear and corrosion resistance.

The light pipe 6 is a conduit for conveying light from the side light source 4 to an area inside the mirror mount 11. The light pipe 7 includes a tightly bundled group of optical fibers encased in stainless steel tubing and bent to conform to the design needs. The output end of the light pipe 6 enters the underside of the mirror mount and points upward and away from the mirror at an inclination angle slightly off vertical. It is positioned so that it casts light at a very shallow angle on the seam. The input end of the light pipe 6 is mounted so that its axis coincides with the radiant axis of the side light source 4.

The direct light source 3 and the side light source 4 are both preferably focused beam lamps of either the incandescent variety or the LED variety. Both have two power leads each, should operate in the voltage range of 0 to 5 volts dc and draw no more than 0.5 amperes. Their brightness should increase with increasing voltage. The beam of each lamp should be focused into a narrow beam of approximately parallel rays for maximum light transmission efficiency. Both light sources are preferably located within the device and positioned to point directly into their respective fiber optic bundles. The radiant axis of the direct light source 3 should coincide with the axis of the input end of the input cable 15 of the ring illuminator 5. The radiant axis of the side light source 4 should coincide with the axis of the input end of light pipe 6. The focused beam diameters of both the two lamps should be sized to match the diameters of the input ends of their respective fiber optic bundles.

The dual voltage power supply 8 is located on the inside of the device and is assembled from a variety of common electronic components including resistors, capacitors, diodes, integrated circuits and transformers that are mounted on a printed circuit board. As inputs it receives 120 Vac or 240 Vac power from the mains and two control signals from the computer interface. It outputs two independently variable voltages which power the two lamps 3,4 and determine their brightness. The circuit portion that receives the control signals from the computer interface is high impedance so draws only a few milliamps of current from the computer or driving device. The output stage of the each power supply channel can supply a current of up to 0.5 amperes at a voltage in the range of 0 to 5 volts depending on an input control voltage which can vary in the range of 0 to 10 volts. The dual voltage power supply has a total of five incoming and four outgoing leads. Two incoming leads are connected to AC line voltage via a power cord. The other three incoming leads are connected to the computer interface 9. Two of the outgoing leads are used to power the direct light source lamp 3. The other two are used to power the side light source lamp 4.

The computer interface 9 is a multi-pin D-shaped connector which carries control signals between the device and the outside world. On one side it is joined directly to input circuitry of the dual voltage power supply 8, on the other it is joined to an external device via an appropriately wired mating connector. The external device can be any device, such as a computer, or voltage controller, which can output a selectable direct current voltage in the range of 0 to 10 volts. Only three of the pins in the interface are connected. Two pins are connected to the direct light control voltage line and the side light control voltage line, respectively, of the input circuits of the dual voltage power supply. The third pin connects to the power supply as the control voltage return. By varying the voltage on either or both these control lines, a connected device may control the brightness of the two light sources in the seam inspection device.

The can platform 12 is a thick surface ground sheet of stainless steel for holding the can in position during inspections. It may be rectangular in shape with a notch cut out of its rear portion to make room for the mirror mount 11. It must be thick enough to prevent any flexing when a can is placed on it. It is mounted horizontally to the front of the base so that it is parallel to the optical axis A—A and at a height which allows a can seam sample to be visible to the camera when a can is placed on the platform.

The enclosure 13 wraps around the base on four sides forming a box like metal shell around the internal components. It enshrouds all components except for the can platform 12, mirror mount 11, and the output end of the light pipe 6. It adds stiffness to the device and serves to protect the internal components from foreign matter and stray light.

To operate the video-based can seam inspection device a can 14 is cut in two places on the end (i.e., bottom or top) of the can 14 (FIG. 1). One cut is made along the radius and toward the center of the can 14— the other is made a slight distance to one side but substantially parallel to the first cut. The material between the two cuts is moved out of the way by pressing it in toward the inside of the can 14, thus, creating an opening in the bottom and side of the can revealing the cross-section of the double seam 16 located around the periphery of the top or bottom of the can. With a portion of the end and side of the can removed, the can is then placed cut side down on the can platform 12 so that the mirror mount 11 enters the inside of the can via the cut away portion of the can 14. The operator moves the can to contact the right side of the mirror mount so that the seam 16 is visible and in focus on the display device. Light from the ring, illuminator 5 and direct light source transmits through the opening in the side of the can and is reflected off the mirror 7 to illuminate the seam. In addition, the output end of the light pipe 6 located within the mirror mount 11 is oriented to transmit light towards the cross-section of the cut in the seam 16 without being reflected off mirror 7. If necessary, the operator then adjusts both the direct light source 3 and side light source 4 intensity levels via the computer interface for the best image of the seam on the display device. The seam may then be visually inspected and/or measured using video cross-hairs or line cursors on the display device. If a computer is interfaced with the seam inspection device, it can be used to automatically store the measurements of an inspection. In addition, optimum settings for both direct light source 3 and side light source 4 intensities can be stored by the computer and recalled instantly, thus making the video-based inspection of a wide variety of seams very fast and simple.

We claim:

1. A seam inspection device comprising:
an optical display device;
means for supporting a container along an optical axis of said optical display device; and
dual means for illuminating a seam on said container.

2. The seam inspection device of claim 1 wherein said dual means for illuminating a seam on said container comprises a side light source and a direct light source.

3. The seam inspection device of claim 2 further comprises a mirror located along said optical axis of the optical display device and oriented at a forty five degree angle relative to said optical axis.

4. The seam inspection device of claim 3 wherein said direct light source illuminates the seam of said container with light directed substantially ninety degrees from said seam.

5. The seam inspection device of claim 4 wherein said side light source illuminates the seam of said container with light directed substantially oriented at a shallow angle to said seam.

6. The seam inspection device of claim 5 wherein said direct light source is oriented to transmit light to a ring illuminator, said ring illuminator coaxially positioned relative to said optical axis to transmit a ring of light towards the seam of said container.

7. The seam inspection device of claim 6 wherein said side light source is oriented to transmit light to a light transmission means capable of transmitting light from said side light source towards the seam of said container at an angle not normal to said seam.

8. The seam inspection device of claim 7 wherein said side light source and said direct light source are controlled by a means for independently varying the intensity of the side light source and direct light source.

9. The seam inspection device of claim 8 wherein the means for independently varying the intensity of the side light source and direct light sources comprises a power supply.

10. The seam inspection device of claim 9 wherein the optical display device comprises an optical imaging device.

* * * * *